Figure 2:
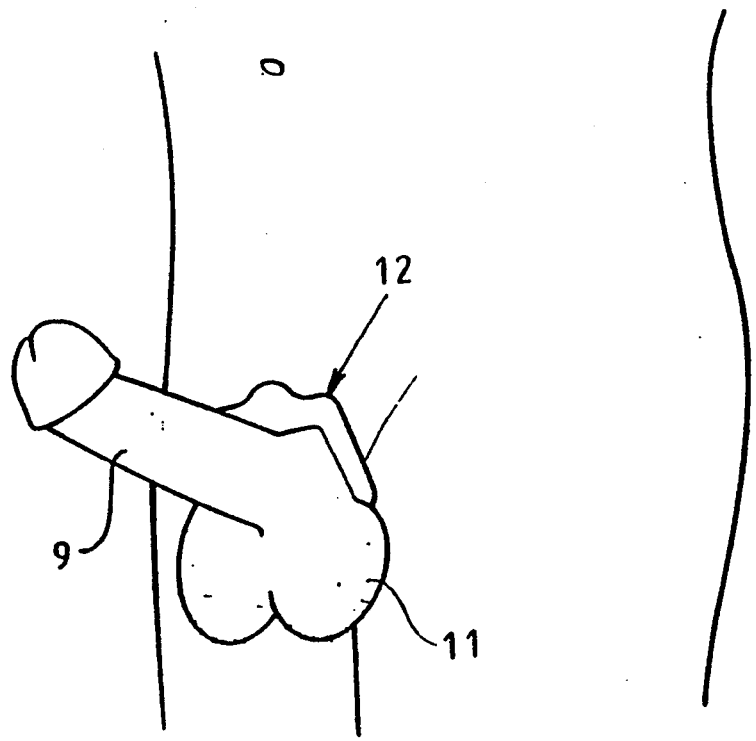

United States Patent [19]

Fischer

[11] Patent Number: 5,439,007
[45] Date of Patent: Aug. 8, 1995

[54] SUSPENSORY

[76] Inventor: Albert G. Fischer, Kohlenbankweg 20, 4600 Dortmund 50, Germany

[21] Appl. No.: 262,857

[22] Filed: Jun. 21, 1994

Related U.S. Application Data

[63] Continuation of Ser. No. 839,252, Mar. 17, 1992, abandoned.

[30] Foreign Application Priority Data

Sep. 3, 1991 [DE] Germany .................. 41 29 177.8

[51] Int. Cl.⁶ ............................................. A61F 6/02
[52] U.S. Cl. ................................. 128/842; 128/885
[58] Field of Search ............... 128/842, 844, 918, 885, 128/886, DIG. 25

[56] References Cited

U.S. PATENT DOCUMENTS

| | | | |
|---|---|---|---|
| 3,147,754 | 9/1964 | Koessler | 128/885 |
| 3,203,421 | 8/1965 | Bialick | 128/885 |
| 4,834,115 | 5/1989 | Stewart | 128/885 |
| 4,942,886 | 7/1990 | Timmons | 128/885 |

FOREIGN PATENT DOCUMENTS

| | | | |
|---|---|---|---|
| 0317730 | 9/1902 | France | 128/885 |
| 0336834 | 5/1921 | Germany | 128/885 |
| 8105304 | 6/1983 | Netherlands | 128/885 |

*Primary Examiner*—Michael A. Brown

[57] ABSTRACT

A suspensory for improving the erection of the human male penis by means of deliberately choking the backflow of the venous blood, including a rigid, generally rectangular ring composed of two crossbars and two sidebars, which, in use, surrounds the penis as well as the scrotum, and which carries one rounded bulge 13 at the center of its upper crossbar that presses on the topside of the penis near the abdomen, and one bulge 17 on or adjacent its lower bar that presses on the root of the penis at the backside of the scrotum. These two bulges 13, 17 are shaped and placed such as to choke all three main veins, the vena dorsalis superficialis and the vena dorsalis profunda penis at the topside of the penis, and the venae profundae penis at the underside of the penis behind the scrotum, including the swell pads and valve flaps contained these veins, such that the arteries and nerve cords of the penis that run parallel to those choked veins are crowded sideways by said bulges into the empty corners of the rectangular ring so that arteries and nerve cords remain essentially unchoked. The lower bulge 17 may be provided on a rearward extension rod 15 which carries a rectal cone.

19 Claims, 3 Drawing Sheets

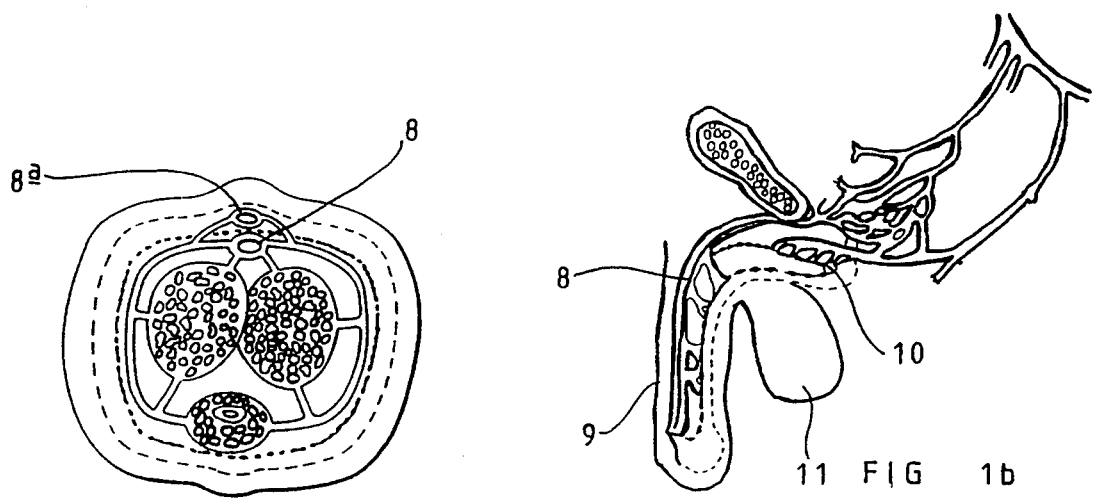
FIG 1a
FIG 1b
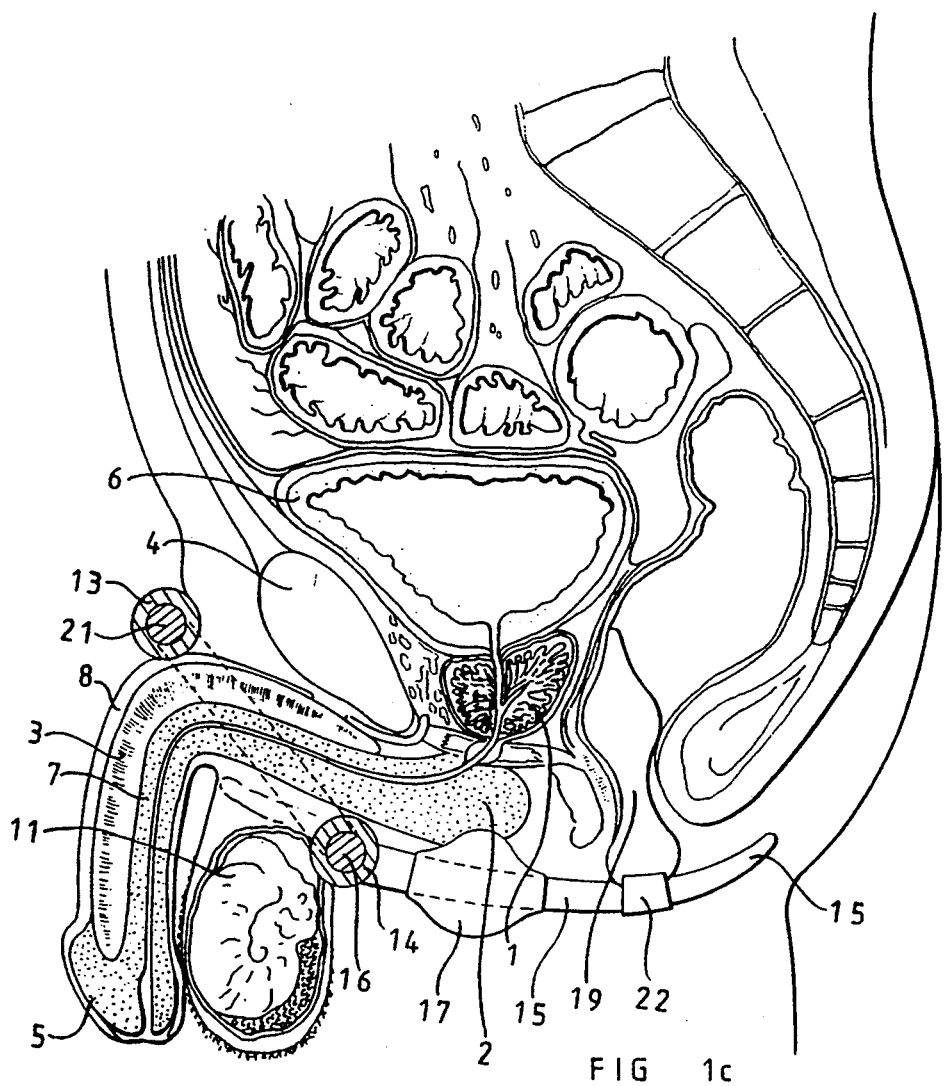
FIG 1c

SUSPENSORY

This application is a continuation of application Ser. No. 07/839,252, filed Mar. 17, 1992, abandoned.

The present invention is concerned with a medical orthopedic device termed a "suspensory" for the symptomatic relief of the widespread male ailment known as "erectile insufficiency", i.e. insufficient attainment and/or insufficient maintenance of the engorgement of the penis called erection as is necessary to achieve an orgasm that is mutually satisfying to the couple. About one third of all grown-up men in the civilized world are more or less afflicted by this infirmity, especially those of middle or older age, but also more and more young men who are exposed to heavy stress.

It is well known that incapability to achieve sexual intercourse may be the cause of severe after effects such as alcoholism, heavy smoking, drug addiction, divorce, job problems, depressions, brutality, suicide. On the other hand it is well known that sexually content couples keep themselves physically and mentally fit and have a positive outlook on life. The suspensory according to the present invention is harmless and inexpensive as compared to the other known impotence therapies listed below. It can also be used by men of normal potency to enhance their sexual prowess, and for the relief of marital monotony with normal couples. Thus it enhances the health of the whole populace.

Up until recently it was thought that psychogenic disturbances were the main cause for erectile impotency. Today it is known, however, that only about 10% of such cases have mental origin. More than half of all physically-induced cases of impotence are based on excessive backflow of the venous blood stream from the erectile tissues due to varicose veins, and/or due to malfunction of the venous swell pads and flaps which acts as backflow valves. About 30% of all impotence cases are caused by insufficient arterial blood supply due to arteriosclerotic obstruction.

Such cases can be cured by the present invention. This invention cannot help, however, with nervous or psychic disorders, malformations, fractures, cancer, bleeding wounds etc., where professional and clinical therapy is indicated (see, e.g., Ref. /1/: H. Porst "Erectile Impotence" (in German), Enke Verlag Stuttgart 1987, DM 82.-).

Also, the present invention cannot cure premature ejaculation as is prevalent in young men.

However, the incapability to achieve orgasm which plagues older men can be relieved by the present invention, thus giving older men a second youth.

Presently, the clinical therapy of impotence proceeds in the following ways:

1) Self-injection of vasoactive chemicals into the erectile tissue of the penis to dilate the arteries, by means of injection needle shortly before coitus. This procedure is, however, unnatural and painful. With frequent repetition there is a risk of hardening of the mutilated penis tissue. With some patients this therapy is without any effect. Contrarily, with about 3% of all patients it results in a permanent erection ("priapism") which requires hospitalisation with danger of gangrene of the penis.

2) Vaso-surgical operations, whereby penis veins are deadened or severed or where clogged arteries are opened, or where an arterial bypass is created from the abdominal cavity to the penis. The rate of success is low, however, and in case of failure the situation is worse than before.

3) Surgical implantation of silicone rubber rods, or of hollow, inflatable silicone rubber vessels into the penis, replacing the corpora cavernosa and spongiosa. The rate of success is quoted as high, but there are no long-term statistics yet as regards the after effects. Further, thereafter there is no engorgement of the glans of the penis, as is required for the intravaginal organism of the female partner. The healing period from the date of implantation to the first usability of the penis is many months. In case of failure of this operation the penis becomes good only for urination. Last but not least, the cost of this operation is in the order of $10,000.

Compared to these invasive therapies the use of the present invention is harmless and inexpensive and does not preclude a surgical solution at a later time.

4) The non-invasive employment of flexible or rigid penis belts on rings (to which category the present invention belongs) is long known. Such rings, usually consisting of elastic rubber, are strapped around the already erect penis. The erection can be produced by means of an evacuated suction jar. The pinch-off encompasses veins, arteries and nerve cords, thus not only stopping the backflow of venous blood which is desired, but also preventing the supply of fresh arterial blood. Shortly after the pinch-off, therefore the penis turns blue and numb, and the circumference where the ring is pinching starts to hurt. The parts of the penis behind the pinch over the scrotum, and in the perineum at the penis root, which are not pinched-off, turn limp, so that the stiff front penis before the pinch-off is dangling down instead of standing up. Therefore, vigorous pushing during coitus is not possible. If orgasm is reached, the ejaculate cannot escape through the choked-off urethra but is emptied backwards into the bladder. All of this is experienced as unnatural and disturbing by both partners. The present invention is much better in these respects.

There are penis belts available which carry special protruding pads claimed to choke the veins on the upper surface of the penis. However, since a tight elastic ring produces a uniform hydrostatic pressure in the deformable penis tissue in the plane of the pinch, such pads are of no use; not only the veins but also the arteries and nerve cords running through the pinch-off plane are choked-off also, such that the effect is the same as with flexible rings having no such special pads, as delineated above.

Further, the important venae profundae penis which lie below the skin in the perineum behind the scrotum, cannot be reached at all by such rings that enclose only the penis and not also the scrotum; if the pinching is not extremely tight the trapped venous blood can escape through these venae profundae penis and the erection fades away since it is known that all penis veins intercommunicate with each other through numerous cross connections.

Patents describing such rings as covered by the above critique are:

Ref. /2/ Osbon, U.S. Pat. No. 4,856,498 (1989)
Ref. /3/ Atchley, U.S. Pat. No. 3,636,948 (1972)
Ref. /4/ Larson, U.S. Pat. No. 2,581,114 (1952), Products according to Ref. /2/ are now marketed worldwide.

The efficacy of these penis rings is surpassed by far by the present invention, see below.

There is also a patent which describes a suspensory which is, formally, similar to the present invention in that it encloses not only the penis but also the scrotum, and which is made of a rigid plastic material with rounded rectangular circumference:

Ref. /5/ Blakoe, Brit. Pat. 531 56/75 (1975), and Blakoe, Swiss. Pat. 612 344 (1979).

Since this Blakoe suspensory could possibly be cited as a prior art against the present invention, its deviations from the present invention will be described here in more detail: In the patent description and also in the instructions for use of this Blakoe ring (which is obtainable from England through mail order), its way of functioning is described: Copper and zinc electrodes which are mounted on the Blakoe ring and which are moistened by the skin sweat (electrolyte) of the man, emit galvanic currents through the penis thus promoting the erection. There is no explanation how this comes about. There is no mention of choking-off of the veins by exertion of pressure as with the present invention. To the contrary, the Blakoe ring is expressly to be fitted loosely, not tightly, around the penis. Besides, our tests with several factory-new Blakoe rings showed that the copper and zinc electrodes on the ring were not in electrical contact with each other, so that even with sweat as electrolyte there existed no closed galvanic circuit (Danjell element) through the penis tissue.

The present invention describes a suspensory to achieve rigid erection of the penis and mutually satisfying orgasms, to help men with erectile insufficiency due to "venous leak".

According to the invention there is provided a suspensory for improving the erection of the human male penis by means of deliberately choking the backflow of the venous blood, consisting of a rigid, generally rectangular ring composed of two crossbars and two sidebars, which, in use, surrounds the penis as well as the scrotum, and which carries one rounded bulge at the centre of its upper crossbar that presses on the topside of the penis near the abdomen, and one bulge on or adjacent its lower bar that presses on the root of the penis at the backside of the scrotum, whereby these two bulges are shaped and placed such as to choke all three main veins, the vena dorsalis superficialis and the vena dorsalis profunda penis at the topside of the penis, and the venae profundae penis at the underside of the penis behind the scrotum, including the swell pads and valve flaps contained these veins, such that the arteries and nerve cords of the penis that run parallel to those choked veins are crowded sideways by said bulges into the empty corners of the rectangular ring so that arteries and nerve cords remain essentially unchoked.

Figures 3A, 3B:
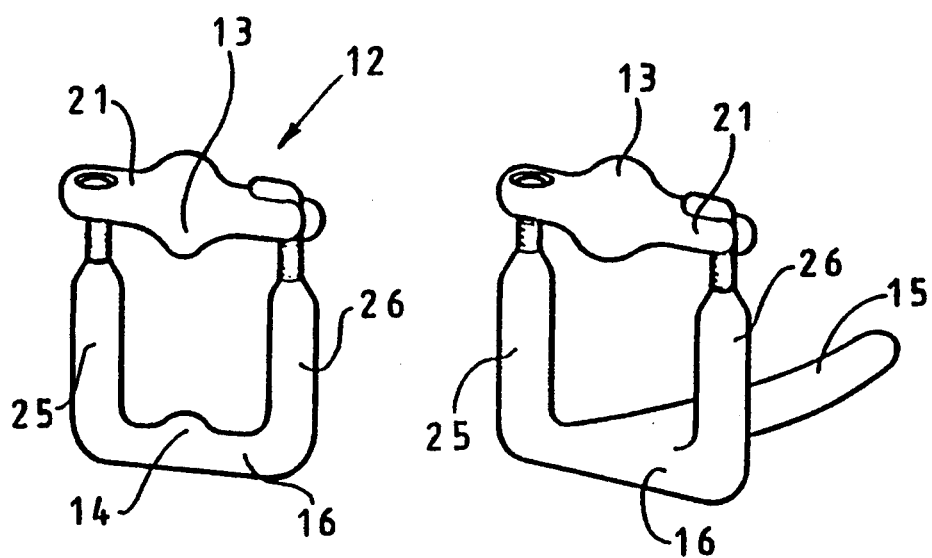
Figure 4:
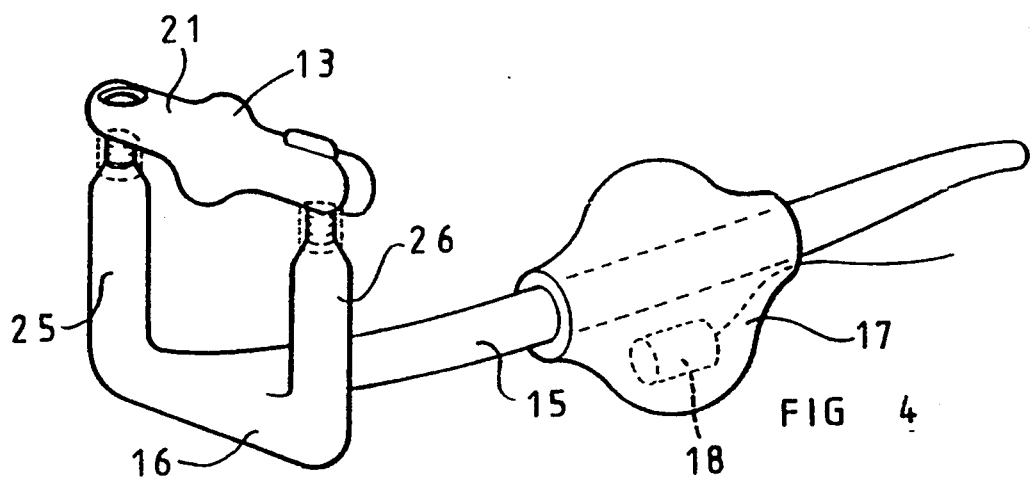
Figure 5:
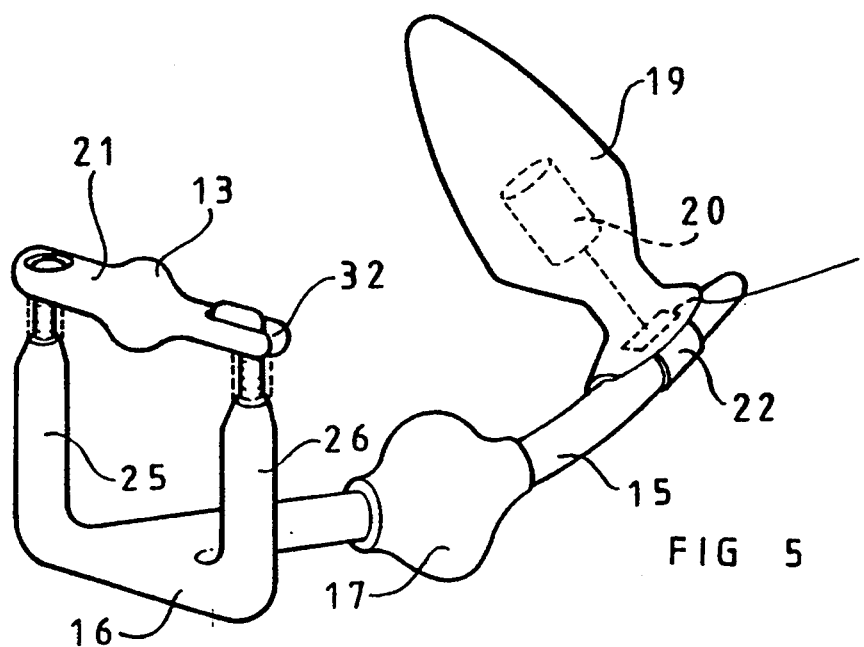
Figure 6:
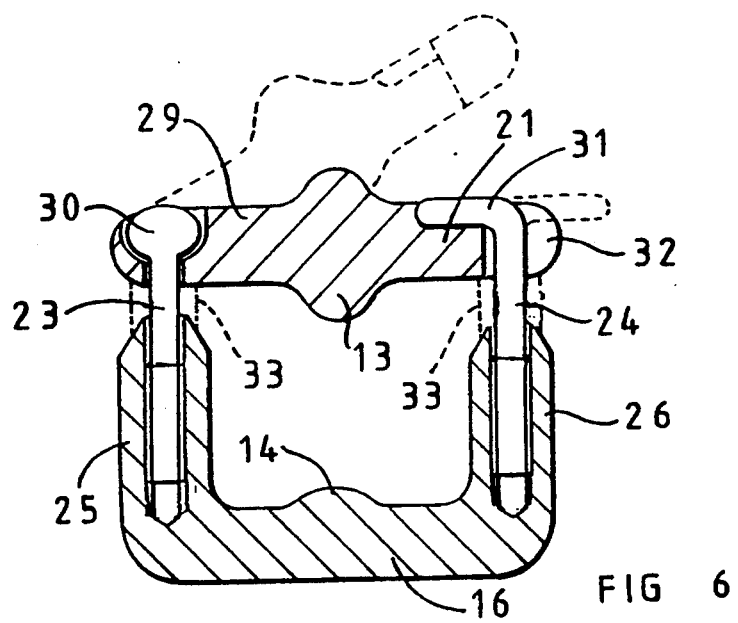

For a better understanding of the invention, reference is made to the required explanatory sketches and preferred embodiments as shown in the accompanying eight drawings, in which:

FIG. 1a is a simplified cross-section of the penis, with main veins,

FIG. 1b is a longitudinal sectional section through the penis, showing the most important drainage veins, FIG. 1c is an anatomic cross-section with cut-off left half of the human body, with full suspensory and rectal cone applied, FIG. 2 is a perspective view of a man's loins with suspensory attached. The extension rod and accessories remain invisible, FIGS. 3a and 3b show a suspensory without and with short extension rod, FIG. 4 shows a suspensory with a long extension rod, and with an optional position-adjustable ball bulge, FIG. 5 shows a suspensory with long extension rod, with an optional adjustable ball bulge, and with rectal cone, both with optional built-in electric vibrators, and FIG. 6 is a front view of a suspensory to show the fastening mechanism, the size-adjustment mechanism, and the shape to prevent skin squeezing.

Contrarily to the suspensories according to the above-mentioned Refs. /2–5/, the suspensory according to the present invention which tightly (in contrast to loosely, Ref. /5/) encloses both penis 9 and scrotum 11, functions by pointedly choking-off the venous backflow of all three main penis veins: venae profundae superficialis 8a, vena dorsalis profunda 8 at the top surface of the penis, and the venae profundae penis 10 at the underside surface at the root of the penis in the perineum behind the scrotum (see FIG. 1a, b).

The anatomic facts can be seen in the textbooks of human anatomy, see e.g. FIG. 1c, which also shows the prostate 1, bulbus corpus spongiosum 2, corpus cavernosus penis 3, os pubis 4, glans penis 5, bladder 6 and corpus spongiosus 7.

The venae profundae penis 10 in the perineum can be squeezed only by the application of pressure to the root of the penis behind the scrotum 11, they cannot be reached at all by those suspensories which enclose only the penis, not the scrotum (Refs. 2–4). Consequently, all the three inflatable corpora of the penis (two corpora cavernosa, one corpus spongiosus) are brought to full erection by the present invention for the first time; the suspensories of Refs. 2–4 were able to erect only the two corpora cavernosa, and these only partially from the front tip to the pinchoff before the scrotum, not in the perineum.

The generally rectangular, rigid shape of the suspensory 12 of this invention (see FIGS. 3–6) was consciously chosen so that only the veins would be choked-off by the bulges 13, 14 in the center on the upper crossbar 21 and the lower crossbar 16, but not the arteries and nerve cords which extend parallel sideways of the veins. This effect is achieved, in the suspensory according to the invention, by the fact that in the plane of the rigid rectangular ring the penis tissue which contains the arteries and nerve cords and which extends parallel to the veins that are compressed by the bulges 13, 14, is shifted by this deformation sideways into the empty corners of the ring where the hydrostatic pressure is so low that these arteries and nerve cords remain largely unsqueezed. Thus the arterial bloodstream is maintained, and the nervous sensations remain undisturbed. Therefore, coitus can now be enjoyed as long as the couple desires. This is impossible with the penis-pinching rings mentioned above. For instance, with the Osbon method (Ref. 2) an upper limit of 30 minutes is recommended, and a warning is issued not to fall asleep as this might cause gangrene of the penis. In contrast, with the suspensory according to the present invention which can be worn indefinitely (and which, by the way, can also be put on or taken off much easier) the woman experiences the penis of her male partner as natural and alive, promptly reacting also to psychic influences (e.g. stimulating words), whereas she would sense his penis, when pinched-off by a tight rubber ring, like an artificial dildo.

By positioning the vein compression bulge 13 on top close to the os pubis 4, and the one 14 on the bottom close to the musculus bulbospongiosis penis at the rear end of the corpus spongiosus 7 in the perineum, the penis is stiffened throughout and stands off 90° from the abdomen, see FIG. 2. Further, the pressure on the veins is exerted just where the disfunctioning swelling pads and backflow valve flaps are located in them (see, e.g. X-ray pictures in Ref. /1/on Page 93). These valved veins require, therefore, only mild pressure for choking, so that the requisite pressure does not have to be as large as would be required to choke-off a smooth vein. Also due to this additional effect the adjacent arteries and nerve cords are not impeded.

In comparison to the rings which enclose only the penis so that the scrotum dangles down loosely between the thighs, the suspensory according to the present invention which encloses also the scrotum 11, tightens the scrotum and shifts it forward visibly (see FIG. 2). This generates the further advantage that, in the normal coital position ("missionary position"), the scrotum is rhythmically touching the labiae of the woman, thus enhancing mutual pleasure and thereby the male erection, and thus promoting the attainment of orgasm.

Further, the rounded external elevation of the upper bulge 13 of the suspensory is enhancing the pleasure of the female partner (and thereby retroactively that of the male, and his erection) by massaging her intensely-innervated urethral opening, and her clitoris.

In particular, a novel rod-shaped extension 15 may be provided normal to the lower crossbar 16 of the suspensory and extending toward the perineum and anus (FIG. 3b). This extension is strongly lust-enhancing, and thereby erection-promoting, for the male. The extension 15 may be in the form of a rod of about 12 mm diameter, which can be straight or also slightly curved following the anatomy of the perineum. The extension 15 chokes the network of the venae profundae penis 10 where it is covered by the muscular layer musculus bulbospongiosus (which is contractible intentionally) and which, additionally, is spiced with the perineal lust nerve network (with individually different strength). This can now be stimulated by the coital thrusting movement, and by means of tensioning the thigh and Po muscles (musculi glutaeus maximus), using the extension rod as a counterpart.

In order to further enhance this lustful effect, a solid bulge or a rubber-elastic hollow ball 17 of 4 to 5 cm diameter with openings on opposing sides (see FIGS. 4 and 5), is placed on the extension rod 15. Its position on the rod is fixed for a solid bulge integral with the rod, or can be optimized by manual shifting for the rubber ball, see FIG. 4. The squeezing of the thigh and Po muscles, for which the ball acts as a counterpart, are transferred by this bulge or ball onto the periheal lust nerve network, thereby creating still more pleasurable sensations that are added to the ones created in the glans of the penis.

This rubber ball can be enhanced, optionally, by a built-in electrical vibrator 18 (see FIG. 4) if the complications due to the requisite extension cable are accepted.

Further, maximal lust enhancement can be optionally achieved if the extension rod is prolonged beyond the anus opening (i.e. about 16–18 cm from the lower crossbar 16 of the ring) and is connected at its rear end with a rectal cone 19 (commercially available in sex shops) made of soft material (see FIG. 5). This rectal cone 19 massages the lust nerve system of the prostate by means of the thrusting movements transferred by the extension rod 15, and by the pressuring created by the tensioned muscles. Optionally, this rectal cone 19 can be enhanced in addition, by another electrical vibrator 20; its extension cable can be unified with that of the vibrator 18.

Thus, according to this invention, it is possible for the first time for the male to experience, during a normal heterosexual coitus, combined simultaneous lust sensations from the glans penis, from the perineal lust nerves, and from the prostate nerves, in analogy to the combined sensations of clitoral and intravaginal (G-point) lust experienced by a sexually fully-articulated female.

The present invention provides, therefore, not only a therapy for the ailment "erectile insufficiency", but also novel lustful experiences which in their intensity by far exceed normaicy, all this being achieved in a natural, harmless, drug-free way, The suspensory according this invention can be realised in stages of increasing complexity and efficacy. In its simplest form it consists of a rectangular, rounded ring with detachable upper crossbar 21, with one bulge 13 in the centre of the upper crossbar and one 14 on the lower crossbar 16, in the same plane of the ring, see FIGS. 3, 6. This ring 12 can be carried by a man conveniently in his trouser pocket.

With the "medium" embodiment, the lower crossbar 16 is extended by a rod 15 normal to the plane of the ring along the perineum, see FIG. 3. By this rod the venae profundae penis 10, here covered by musculus bulbospongiosus, are compressed, which can be enhanced by a ball 17 and by conscious contractions of this muscle group, thereby additionally stimulating the perineal lust nerve network during coitus. If desired, an electrical vibrator 18 can be incorporated into the ball.

With the "grand" version, additionally a rectal cone 19, which after greasing with lubricant is introduced into the rectum, can be added to the rear end of the extension rod 15 by means of a simple magnetic coupling 22, See FIG. 5. It excites the prostatic nerves by means of the motions of the penis that are transferred to it by the extension rod, and by the muscle contractions. Also here, another electric vibrator 20 can be incorporated optionally.

With this version of the suspensory, permitting the addition of glans, periheal and prostatic lust, even a fatigued and worn-out man can achieve a strong orgasm which is mutually satisfying. With a well-rested man the stimulation may be so strong that his orgasm occurs prematurely so that the female partner cannot follow. This suspensory permits and requires, therefore, Self-control and a full scale of adjustments to the respective situation; the more tired the man, the more stimulation is needed, and vice versa.

As pictured in FIGS. 1–5, the suspensory according to this invention consists of two parts (upper and lower part) made of plastic resin (e.g. PE, PA, PVC, Epoxy, etc.), with connecting members 23, 24 of metal (brass, aluminum, stainless steel) or also of resin, which can be mass produced by methods well known in the art. The prototypes were made by hand from resin blocks; this suspensory could have been made from wood since antiquity had the principle been known then!

Depending on the combined thickness of penis and scrotum of the respective individual, the inner distance from upper 13 to lower bulge 14 is 20–50 mm, and from right to left side bar 25, 26 40–60 mm. Accordingly, three main sizes of the suspensory, small, medium and large, are manufactured, from which each man can select the one that fits him approximately. This he can then fine-adjust by plus or minus 8 mm by turning the threaded connection rods 23, 24 (without tools), as described later below.

The diameters of the bulges 13, 14 on the upper and lower bars are about 10 mm thicker than that of the bars themselves; in the simplest version of the suspensory they are opposite each other in the same plane.

The versions with a rearward extension rod 15 on the lower crossbar 16 (FIGS. 3–5) no longer have the lower bulge 14 on the lower crossbar but on this extension rod, about 3–8 cm behind the plane of the ring, for choking the venae profundae penis behind the scrotum at this position where they are covered by the contractible layer of the musculus bulbospongiosus that is permeated by the perineal lust nerves. This bulge can be a solid part of the extension rod. However, this lower bulge is preferably implemented by means of the small perforated rubber ball 17 that can be shifted manually to the best position on the extension rod. If this manually adjustable elastomer ball of 3–5 cm diameter for choking the veins venae profundae and for stimulation of the perineal lust nerves is used, then the extension rod 15, on which it glides, should extend beyond the anus (about 18 cm), as shown in FIGS. 4,5 so that the ball 17 cannot fall off unintentionally.

The optional rectal cone 19 for stimulating the prostate (FIG. 5) is obtainable commercially and consists of smooth, soft resin with foam filling, with a soft flat end plate. Onto that a flat permanent magnet 27 (see FIG. 1c) is glued, so that this rectal cone, after having been introduced into the rectum manually following copious lubrication, couples self-seeking to the rear end of the extension rod which contains, for that purpose, a piece of magnetic iron 28, e.g. a threaded steel screw. This self-seeking magnetic connector can be disconnected, for taking off the suspensory, by applying mild force. By this connector the coital thrusts and vibrations are efficiently transferred to the rectal cone so that it can stimulate the prostate, in addition to the squeezing that it applies to the prostate due to tightening of the muscles.

In order that the man can easily and quickly put on or take off the suspensory, the loose upper crossbar 29 is attached to the lower, U-shaped part of the suspensory at the one side of the U by means of a loose universal joint 30, so that it can be swung open sideways and upwards. At the other end of the crossbar there is a simple locking mechanism 31 which is closed manually by compression and latching. This arrangement also permits individual size adjustment to obtain a tight fit, simply by turning the two threaded bolts 23, 24 and it is shaped such that there cannot be painful squeezing of the skin.

The preferred embodiment is shown in FIG. 6, but other solutions are easily conceived. For example, we examined a mechanism where the upper crossbar is swung open sideways by turning it normal to the plane of the ring, or another one where it is connected to the lower part of the suspensory by means of adjustable rubber bands.

The mechanism must be simple yet permit size adjustment, without skin squeezing, and without opening unintentionally.

With the preferred mechanism, both sidebars 25, 26 of the U-shaped lower part of the suspensory contain, lengthwise, threaded bores (e.g. M6), which extend deep until to the lower crossbar. In each bore there is placed a threaded bolt 23, 24 (e.g. brassy M6). The threads of these bolts are absent on the parts of the bolts which emerge from the side bars, so that they have smooth, polished cylindrical surfaces there. One bolt, e.g. the left one 23, has a rounded head 30 which fits into the funnel-shaped bore at the left end of the upper crossbar 29, so that this can be swung to all sides but cannot escape upwards. This is the aforementioned loose universal joint. The other bolt 24, e.g. the right one, has no head but its upper smooth cylindrical end 31 is bent perpendicularly for about 10 mm, like the handle of a walking cane.

In order to close the movable upper crossbar 29 against the sidebars 25, 26 of the lower part of the suspensory, against the pressure of the closed-in penis-scrotum tissue, the handle 31 of this right bolt 24 is turned outwardly in the direction of the ring plane, and the loose upper crossbar 29, which at its right end has a slot 32 of about 7 mm width from its outer edge inwardly, is pressed downward from above onto the handle 31 until this handle emerges on the upper surface of the crossbar 29. Then the handle is turned inwardly through 180 degrees by thumb and forefinger, where it sinks into a shallow furrow (about 3 mm deep) that is provided there. The spring force is supplied by the compressed penis scrotum tissue. In this way the suspensory is now firmly latched around penis and scrotum.

For taking off the suspensory, the movable upper crossbar 29 is pressed down on its right side against the lower part of the suspensory by thumb and forefinger, against the spring force of the compressed tissue, until the handle 31 emerges from its furrow. Then the handle is turned by 180 degrees outwardly so that it can slip through the slot 32. The upper crossbar now flips open on its right side. The suspensory can now be taken off by moving it downward towards the thighs. With some practice, all this can be done quickly in the dark.

For size-adjustment and obtaining a proper fit of the suspensory to the penis-scrotum tissue, both the two metal bolts 23, 24 are turned by thumb and forefinger by an equal number of turns right (tighter) or left (looser). If the suspensory is put on too tightly, it creates pinching pain. If it is fitted too loosely, it becomes ineffective and the erection fades away. Thus, depending on one's daily state of personal fitness, one can adjust the pressure of the suspensory optimally.

With some practice also, this fitting can be accomplished on the body without taking the dispensory off.

To avoid painful skin squeezing, the upper end faces of the sidebars 25, 26 of the lower, U-shaped part of the suspensory are not shaped in the form of planar surfaces perpendicular to their length, but are cone-shaped radially to the central threaded bore. The cone angle against the central axis should be larger than 45 degrees, preferably 60 degrees. In this way, there are no planar surfaces that move toward each other with skin squeezed in between. Now the skin glides along the smoothly polished shaft and cone surfaces unsqueezed.

In order to avoid too hard pressuring of the skin against these 5 mm thin cylindric shafts, they can be covered by short pieces of soft, thick-walled latex rubber hose 33, (FIG. 6) to relieve the specific pressure there.

Use of the suspensory is simple and safe. After about 10 repetitions, all moves can be carried out quickly in the dark. To put on the suspensory (it should be lubricated before with jelly to minimise skin friction) the man lifts it upward, using both hands, from below behind the scrotum, whereby the sidebars glide left and right up the scrotum. The handle 31 of the latching bolt is turned outwardly.

After pushing aside the skin folds with the fingers, the right end of the upper cross bar 29 is pressed down with its slot over the handle on the lower U-shaped part by using thumb and forefinger, until the handle 31 emerges on the topside of the slot. Then the handle is turned 180° so that it can sink into the shallow furrow there.

The still flaccid penis is now engorging due to the choked-off outflow of the venous blood while the arterial blood is flowing in. Most of the time, suitable stimulation of the glans lust nerves is required to reach full erection. (Incidentally, contrary to widespread opinion it is possible to introduce the still flaccid penis into the vagina of the cooperating female with the aid of the fingers. The woman then enjoys the engorgement of the penis in her vagina as part of the foreplay).

If, however, the situation requires a hard erection and immediate full vaginal penetration, then the flaccid penis, still without suspensory, can be pumped up within a minute by means of the one of the commercially-available vacuum cup devices which suck the blood into the penis rapidly. (For better vacuum seal, the pubic hair should be cut short and lubricated with jelly). After attaining full erection and removing the suction jar, the suspensory has to be put on now without delay, otherwise the erect penis turns limp owing to the venous leak. Once the suspensory is put on, however, the remaining erection is upheld for a long time, and is enhanced to full hardness by inflow of arterial blood by the lustful stimulation during coitus.

Mostly, however, the employment of a vacuum suction device to obtain a full erection is an unnecessary complication, for, contrary to the penis-pinch-off methods initially described (Ref. /5/), the attainment of full erection is now possible by natural means due to the present invention.

The suspensory, and its accessories, permit a high degree of flexibility and variability in use. For instance, the application, or the removal, of the rubber ball 17 on the extension rod 15 to act as a lower bulge, can be accomplished before or after the attachment of the suspensory. Likewise, the implementation or the extraction of the rectal cone 19, including coupling it to the extension rod, call be achieved before or after the attachment of the suspensory. The simplest version of the suspensory, the small ring without extension rod, can be put on in bed secretly without the female noticing it once she has been pleased, she will become convinced and most likely to accept also the medium and grand versions. For reasons of hygiene, the suspensory and its accessories should be disinfected after each use. The simplest way is washing in warm soapy water. More thorough is spraying with a clinical disinfectant. Safest is immersion in boiling water.

The present invention fills an urgent human need. On the one hand, due to better medical care and better socio-economic conditions, people in the civilised countries reach a greater age and have more free spare time than in former times. Due to progress in birth control methods, women are liberated from old tabus and moral barriers, assume liberal attitudes and develop their sexuality to the fullest just like men.

On the other hand, the old knowledge now becomes manifest that male sexuality is much more frail than that of women since success depends crucially on achieving and long-time maintaining a sturdy erection, and that a large part of the male population (about one third) is more or less impotent, at least some of the time, particularly at middle or greater age. After some failures, coupled with derision by women, men fear sex and withdraw. For each unhappy impotent male there is, statistically, a dissatisfied irritable woman. This millionfold dissatisfaction manifests itself in countless psychogenerated ailments, frictions, struggles, illnesses and animosities.

With the present invention, innumerable persons who, so far, were excluded from full enjoyment of physical life can now rejoice, can find a sex partner, can gain a positive attitude to life and thus overall better health. Compared to the other known therapies of male impotence, the present invention is efficient, inexpensive and harmless, a bonanza to public health.

Sex is humanity's most irrepressible vital urge. Therefore, for the containment of the worldwide spreading new deadly AIDS disease (as well as for the other known, less dangerous venereal diseases) it is imperative that the percentage of happy, stable monogamous couples, as opposed to instable unhappy polygamous singles, is promoted. The present invention is a contribution in this direction.

I claim:

1. A suspensory for improving the erection of the human male penis by means of deliberately chocking the backflow of the venous blood, consisting of a rigid, generally rectangular ring composed of two cross bars and two sidebars, which, in use, surrounds the penis as well as the scrotum, and which carries an upper vein compression bulge in the form of one downwardly protruding rounded bulge at the centre of its upper crossbar that presses on the topside of the penis near the abdomen, and a lower vein compression bulge in the form of one bulge protruding upwardly on or adjacent its lower bar that presses on the root of the penis at the backside of the scrotum, whereby these two bulges extend toward each other and are shaped and placed such as to choke all three main veins, the vena dorsalis superficialis and the vena dorsalis profunda penis at the topside of the penis, and the venae profundae penis at the underside of the penis behind the scrotum, including the swell pads and valve flaps contained in these veins, such that the arteries and nerve cords of the penis that run parallel to those chocked veins are crowded sideways by said bulges into the empty corners of the rectangular ring so that arteries and nerve cords remain essentially unchoked.

2. A suspensory according to claim 1, wherein the crossbars and sidebars are of generally circular cross-section.

3. A suspensory according to claim 1, in which onto the lower crossbar that touches the underside of the penis behind the scrotum there is firmly attached a rigid, straight or slightly upwardly-curved extension rod which extends normal to the plane of the ring over the perineum toward the anus, in use, and where this extension rod carries said lower vein compression bulge for chocking the venae profundae penis of the perineum which are covered there by the muscular layer musculus bulbospongiousus that contains the perineal lust nerves, so that, in addition, this lower bulge can stimulate these perineal lust nerves by being squeezed onto them by the contracting muscles during the coital movements.

4. A suspensory according to claim 3, wherein said lower vein compression bulge is a solid integral part of the said extension rod.

5. A suspensory according to claim 3, wherein said lower vein compression bulge comprises a separate element mounted on the extension rod and adjustable longitudinally thereof.

6. A suspensory according to claim 5, wherein said separate element is in the form of a ball of rubber or other resiliently flexible material.

7. A suspensory according to claim 3, wherein said lower vein compression bulge contains an electrical vibrator.

8. Suspensory according to claim 3, wherein the extension rod is connected to a rectal cone which, in use, is placed in the rectum to stimulate the prostatic lust nerves there by way of the coital movements.

9. A suspensory according to claim 8, wherein the rectal cone is connected to the extension rod by a detachable magnetic coupling.

10. A suspensory according to claim 8, wherein the rectal cone contains an electrical vibrator.

11. A suspensory according to claim 10, wherein the upper crossbar is connected to the two sidebars by respective bolts passing through the ends of the crossbar and screw-threaded into the sidebars, at least one of said bolts being detachable from the crossbar whereby the crossbar may be displaced with respect to the sidebars to facilitate fitting of the suspensory.

12. A suspensory according to claim 11, wherein one of said bolts has a rounded screw head received in a recess at one end of the upper crossbar, so as to retain the crossbar while allowing it to move, and the other bolt has a shaped handle which may be rotated into an out of register with a cooperating slot in the upper crossbar, whereby the shaped handle normally retains the crossbar but allows displacement of the crossbar when the shaped handle is rotated into register with the slot.

13. A suspensory according to claim 12, wherein the upper crossbar is formed with a groove which receives said shaped handle when it is out of register with said slot in the crossbar.

14. A suspensory according to claim 13, wherein at lease one of said bolts has an exposed portion between its respective sidebar and said upper crossbar, whereby the upper crossbar may be pressed towards the lower crossbar to allow release of said shaped handle from the groove in the upper crossbar.

15. A suspensory according to claim 11, wherein said bolts have exposed portions between the respective sidebars and the upper crossbar, and may be screwed into or out of the sidebars to effect adjustment of the size of the suspensory.

16. A suspensory according to claim 15, wherein said exposed portions of the bolts are non-threaded.

17. A suspensory according to claim 15, wherein the exposed portions of the bolts are enclosed by sleeves of soft rubber or other flexible material.

18. A suspensory according to any of claim 15, wherein the upper ends of the sidebars from which the exposed portions of the bolts protrude taper upwardly and inwardly towards the bolts in a general cone-shape.

19. Suspensory for curing the weakness of penis erection by choking the venous backflow, using a rigid ring made of bars with rounded cross sections and with variable circumference:
   a) said ring consists of a cross bar and a side bar;
   b) an essentially rectangular area surrounded by said ring for receiving the penis near the abdomen;
   c) means for movable positioning said upper cross bar at the upper side of the penis;
   d) said upper cross bar and said lower cross bar each have a bulge extending into said rectangular area for choking the backflow of venous blood by pressing on the top side and the bottom side of the penis;
   e) a rod shaped extension carried by said lower cross bar to extend in the perineum area when in use the lower cross bar is positioned under the penis behind the scrotum;
   f) said rod shaped extension having a curved extension rod which stretches across the perineum toward the anus, penetrating through anus and rectum up to the wall of the prostate.

* * * * *